US008273070B2

(12) United States Patent
Inoue et al.

(10) Patent No.: US 8,273,070 B2
(45) Date of Patent: Sep. 25, 2012

(54) PORT MEMBER FOR INFUSION SOLUTION BAG, AND INFUSION SOLUTION BAG

(75) Inventors: Fujio Inoue, Naruto (JP); Isamu Tateishi, Naruto (JP); Tatsuro Tsuruoka, Naruto (JP)

(73) Assignee: Otsuka Pharmaceutical Factory, Inc. (JP)

( * ) Notice: Subject to any disclaimer, the term of this patent is extended or adjusted under 35 U.S.C. 154(b) by 251 days.

(21) Appl. No.: 12/528,062

(22) PCT Filed: Feb. 20, 2008

(86) PCT No.: PCT/JP2008/052847

§ 371 (c)(1), (2), (4) Date: Nov. 24, 2009

(87) PCT Pub. No.: WO2008/102802

PCT Pub. Date: Aug. 28, 2008

(65) Prior Publication Data

US 2010/0094242 A1 Apr. 15, 2010

(30) Foreign Application Priority Data

Feb. 23, 2007 (JP) ................................ 2007-044168

(51) Int. Cl.
*A61B 19/00* (2006.01)

(52) U.S. Cl. ........ 604/408; 604/403; 604/410; 604/411; 604/415; 604/416

(58) Field of Classification Search .................. 604/403, 604/408, 410, 411, 415, 416
See application file for complete search history.

(56) References Cited

U.S. PATENT DOCUMENTS 7,354,426 B2 * 4/2008 Young .......................... 604/403

FOREIGN PATENT DOCUMENTS

JP UM-A-Sho-59-116033 6/1984
JP A-2001-017513 1/2001
JP A-2003-220117 8/2003
JP UM-2005-10046 11/2005

* cited by examiner

*Primary Examiner* — Tatyana Zalukaeva
*Assistant Examiner* — Ginger T Chapman
(74) *Attorney, Agent, or Firm* — Berliner & Associates

(57) ABSTRACT

Provided a port member for an infusion solution bag that is capable of suppressing occurrence of gaps or wrinkles in a sealed portion in a manufacturing process, and preventing damages to resin sheets of a bag body during storage or transportation. A port member for an infusion solution bag includes a tubular body portion having one end sealed by a plug member structured to enable a hollow needle to be pierced into the plug member, and a tubular to-be-sealed portion continuously formed with an other end of the body portion and having an inner space communicated with the inside of the body portion, the to-be-sealed portion being held between and sealed to end portions of resin sheets overlapped together to form a bag body having an inner space for accommodation of at least a medicine, in which the to-be-sealed portion thus sealed has a radially flattened shape.

9 Claims, 11 Drawing Sheets

120
112
115
114
113
200
201
202
20
21
210
211
212
213
A
110
111

PORT MEMBER FOR INFUSION SOLUTION BAG, AND INFUSION SOLUTION BAG

FIELD OF THE INVENTION

The present invention relates to a port member for an infusion solution bag that is fluidly connected to a bag body having an inner space for accommodation of at least a medicine, and an infusion solution bag provided with the port member.

RELATED ART

Various types of container for accommodation of various medicines have been hitherto provided, and among of which, an infusion solution bag 5 that includes a bag body 50 having an inner space 500 formed by sealing end portions (outer peripheral end portions) of resin sheets S, S overlapped each other for accommodation of at least a medicine, and a port member 51 provided fluidly connected to the bag body 50 is known, as shown in FIG. 11(*a*).

The port member 51 includes a tubular body portion 511 that has one end plugged by a plug member 510 structured to enable a hollow needle N to be pierced thereinto, and a cylindrical tube shaped to-be-sealed portion 512 continuously formed with the other end of the body portion 511 and having an inner space communicated with the inside of the body portion 511.

As shown in FIG. 11(*b*), the port member 51 is fluidly connected to the bag body 50 by sealing the to-be-sealed portion 512 to end portions E, E of the resin sheets S, S overlapped to form the bag body 50, while having the to-be-sealed portion 512 held between the end portions E, E of the resin sheets S, S. Specifically, the port member 51 is attached to the bag body 50 to allow the bag body 511 to be communicated with an inner space 500 of the bag body 50 via the to-be-sealed portion 12, by fluid-tightly sealing the to-be-sealed portion 512 to the two resin sheets S, S while having the to-be-sealed portion 512 held between the end portions E, E of the resin sheets S, S, at the time when the end portions E, E of the overlapped resin sheets S, S are sealed together to form the bag body 50.

Whereby, the thus structured infusion solution bag 5 is designed so that the hollow needle N is pierced into the plug member 510, thereby enabling a medicine to be discharged from the bag body 50 or injected into the bag body 50, via the hollow needle N (cf. e.g., Patent Document 1).

Patent Document 1: Japanese Registered Utility Model No. 3118911

DISCLOSURE OF THE INVENTION

Problems to be Solved by the Invention

Meanwhile, the thus structured infusion solution bag 5, which has the to-be-sealed portion 512 (a portion to which the resin sheets S, S are sealed) of the port member 51 formed into a cylindrical tube shape, causes portions of the resin sheets S, S, which portions correspond in position to the to-be-sealed portion 512, to be greatly projected (deformed) along the shape of the to-be-sealed portion 512.

Consequently, wrinkles W may be caused in the resin sheets S, S along boundaries between the sealed portion of the resin sheets S, S, and the sealed portion of the resin sheets S, S and the to-be-sealed portion 512 or in the periphery of the boundaries (cf. FIG. 11(*a*)), or minute gaps G may be formed (cf. FIG. 11(*b*)). This may cause not only poor appearance as a product but also leakage of a medicine through the wrinkles W or the gaps G.

Since the bag body 50 is made of flexible resin sheets S, S, the bag body 50 with a medicine contained therein is sometimes held in folded state (e.g., two folded state) when the infusion solution bag 5 is stored or transported. Since the to-be-sealed portion 512 has a cylindrical tube shape, a portion EP of the to-be-sealed portion 512 corresponding to opening edge portions of the to-be-sealed portion 512 is held projecting (causing an angular projection), so that the projecting portion EP partially contacts a portion corresponding thereto by folding the bag body 50, which may cause rupture of the resin sheets S, S.

In consideration of the above circumstances, it is an object of the present invention to provide a port member for an infusion solution bag, and an infusion solution bag that are capable of preventing occurrence of gaps or wrinkles in a sealed portion in a manufacturing process, and preventing damages to resin sheets of a bag body during storage or transportation.

Means for Solving Problems

According to the present invention, there is provided a port member for an infusion solution bag that includes a tubular body portion having one end plugged by a plug member structured to enable a hollow needle to be pierced into the plug member, and a tubular to-be-sealed portion continuously formed with an other end of the body portion and having an inner space communicated with the inside of the body portion, the to-be-sealed portion being held between and sealed to end portions of resin sheets overlapped together to form a bag body having an inner space for accommodation of at least a medicine, in which the to-be-sealed portion thus sealed has a radially flattened shape. By the "resin sheets overlapped" is herein meant to include two separate resin sheets overlapped, as well as one resin sheet folded along the ridge line into two overlapped sheet sections.

According to the port member for an infusion solution bag, the to-be-sealed portion has a radially flattened shape to have curved surfaces having large curvature radius or substantially flat surfaces, and portions having very small curvature radius. That is, the to-be-sealed portion is formed to have a major axis (between the portions having small curvature radius) and a minor axis (between the curved surfaces having large curvature radius or portions shaped into substantially flat surface). Therefore, when the to-be-sealed portion is held between the end portions of the resin sheets from the opposite sides in the direction of the minor axis of the to-be-sealed portion, the resin sheets are sealed together in a substantially flat state in a direction in which the edges of the end portions of the resin sheets extend. Consequently, it is possible to suppress occurrence of gaps or wrinkles along boundaries between the sealed portions of the resin sheets, and the sealed portion of the resin sheets and the to-be-sealed portion.

Since an infusion solution bag provided with the thus structured port member eliminates a greatly projecting portion due to the radially flattened shape of the to-be-sealed portion of the port member, it is possible to suppress partial contact between the end portions of the port member (end portion of the to-be-sealed portion) and its corresponding portion when the bag body is held folded during storage or transportation, and hence suppress rupture of the resin sheets.

According to another aspect of the present invention, there is provided a port member for an infusion solution bag that includes a tubular body portion having one end plugged by a plug member structured to enable a hollow needle to be pierced into the plug member, and a tubular to-be-sealed portion continuously formed with an other end of the body portion and having an inner space communicated with the inside of the body portion, the to-be-sealed portion being held between and sealed to end portions of resin sheets overlapped together to form a bag body having an inner space for accommodation of at least a medicine, in which the to-be-sealed portion is radially deformable. By the "resin sheets overlapped" is herein meant to include two separate resin sheets overlapped, as well as one resin sheet folded along the ridge line into two overlapped sheet sections.

According to the port member for an infusion solution bag, the tubular to-be-sealed portion continuously formed with an other end of the tubular body portion having the one end sealed with the plug member is radially deformable. Therefore, when the to-be-sealed portion is sealed while being held between the end portions of the resin sheets (with pressing in a radial direction), the to-be-sealed portion is sealed to the resin sheets while being held flat in the radial direction.

Whereby, the to-be-sealed portion has, along its peripheral direction, curved surfaces having large curvature radius or substantially flat surfaces, and portions having very small curvature radius. In other words, the to-be-sealed portion is formed to have a major axis (between the portions having small curvature radius) and a minor axis (between the curved surfaces having large curvature radius or between portions shaped into substantially flat surface). Thus, the resin sheets are sealed together in a substantially flat state in a direction in which the edges of the end portions of the resin sheets extend. Consequently, it is possible to suppress occurrence of gaps or wrinkles along boundaries between the sealed portion of the resin sheets, and the sealed portion of the resin sheets and the to-be-sealed portion.

Since an infusion solution bag provided with the thus structured port member eliminates a greatly projecting portion by forming the to-be-sealed portion of the port member into a flat shape, it is possible to suppress partial contact between the end portions of the port member (end portion of the to-be-sealed portion) and its corresponding portion when the bag body is held folded during storage or transportation, and hence suppress rupture of the resin sheets.

In this case, the to-be-sealed portion is preferably formed with a thinner wall than the body portion to be radially deformable. With this, it is possible to increase the rigidity of the body portion while making the to-be-sealed portion radially deformable, which can prevent a hollow needle from being pierced through the body portion.

As one form of the present invention, the length of the body portion between one end and the other end is preferably longer than the entire length of the hollow needle. With this, a leading end of the hollow needle which has been pierced through the plug member does not reach the to-be-sealed portion, and hence erroneous piercing of the hollow needle into a portion in which the bag body exists can be prevented.

Especially, when the to-be-sealed portion is formed with a thin wall, a hollow needle may be easily pierced through the to-be-sealed portion if it reaches and pierces into the to-be-sealed portion. However, as described above, since the hollow needle does not reach the sealed portion, such event can be prevented.

The body portion and the plug member are preferably formed by double molding. By this, the body portion is held in tight contact with the plug member, and therefore the plugging performance of the plug member to the one end of the body part is enhanced, while also allowing piercing of a hollow needle. By the "double molding" is herein meant to mold previously any one of the body portion and the plug member and then mold the residual one with a material different from the material of the previously molded one so as to bring the residual one into tight contact with the previously molded one. That is, the double molding is achieved, for example, by molding a plug member by curing a molding material filled in one end of a previously molded body portion, or molding a body portion by placing a previously molded plug member into a molding die and then curing a molding material filled between the plug member and the molding die.

According to still another aspect of the present invention, there is provided an infusion solution bag that includes a bag body formed with resin sheets overlapped and sealed together along end portions of the resin sheets, thereby forming an inner space in the bag body for accommodation of at least a medicine, a port member fluidly connected to the bag body, the port member including a tubular body portion having one end plugged by a plug member structured to enable a hollow needle to be pierced into the plug member, and a tubular to-be-sealed portion continuously formed with an other end of the body portion and having an inner space communicated with the inside of the body portion, the to-be-sealed portion being held between and sealed to end portions of the resin sheets overlapped together, in which the to-be-sealed portion thus sealed has a radially flattened shape and is held between and sealed to the end portions of the resin sheets from the opposite sides in the direction of a minor axis of the to-be-sealed portion. By the "resin sheets overlapped" is herein meant to include two separate resin sheets overlapped, as well as one resin sheet folded along the ridge line into two sheet sections overlapped.

According to the thus structured infusion solution bag, the to-be-sealed portion has a radially flattened shape to have curved surfaces having large curvature radius or substantially flat surfaces and portions having very small curvature radius in the circumferential direction of the to-be-sealed portion. That is, the to-be-sealed portion is formed to have a major axis (between the portions having small curvature radius) and a minor axis (between the curved surfaces having large curvature radius or portions shaped into substantially flat surface). Therefore, when the to-be-sealed portion is held between and sealed to the end portions of the resin sheets from the opposite sides in the direction of a minor axis of the to-be-sealed portion, the resin sheets are sealed together in a substantially flat state in a direction in which the edges of the end portions of the resin sheets extend. Consequently, it is possible to prevent occurrence of gaps or wrinkles along boundaries between the sealed portion of the resin sheets, and the sealed portion of the resin sheets and the to-be-sealed portion.

As described above, since an infusion solution bag provided with the thus structured port member eliminates a greatly projecting portion due to the radially flattened shape of the to-be-sealed portion of the port member, it is possible to suppress partial contact between the end portions of the port member (end portion of the to-be-sealed portion) and its corresponding portion when the bag body is held folded during storage or transportation, and hence suppress rupture of the resin sheets.

As one form of the present invention, the length of the body portion between one end and the other end is preferably longer than the entire length of the hollow needle. With this, a leading end of the hollow needle which has been pierced into the plug member does not reach the to-be-sealed portion, and hence erroneous piercing of the hollow needle into a portion in which the bag body exists can be prevented.

Advantages of the Invention

According to the port member for an infusion solution bag and an infusion solution bag, of the present invention, it is possible to suppress occurrence of gaps or wrinkles in a sealed portion in a manufacturing process, and suppress damages to resin sheets of a bag body during storage or transportation.

DESCRIPTION OF THE REFERENCE NUMERALS

1: infusion solution bag, 10: bag body, 11: port member, 20: first molding die, 21: second molding die, 100: inner space, 100*a*: first chamber, 100*b*: second chamber, 100*c*: third chamber, 101: first weak seal portion, 102: second weak seal portion, 102*a*: easy-to-open portion, 102*b*, 102*b*: straight portions, 103: gas barrier film, 110: plug member, 111: body portion, 112: to-be-sealed portion, 112*a*: portion having large curvature radius or portions shaped into substantially flat surface, 112*b*: portion having small curvature radius, 113: to-be-plugged portion, 114: connection tube portion, 115: deformed tube portion, 120: tube body, 200: molding projection, 201: bar-shaped portion, 210: mold, 211: discharge port, 212: fit-in portion, 213: stopper portion, A: space, E1, E2, E1' and E2': end portions, E3, E4, E3' and E4': end portions (lateral side end portions), N: hollow needle, S: resin sheet, α: angle

DETAILED DESCRIPTION OF THE PREFERRED EMBODIMENT

Now, the description will be made for a first embodiment of the present invention with reference to the drawings attached hereto.

Figure 1:
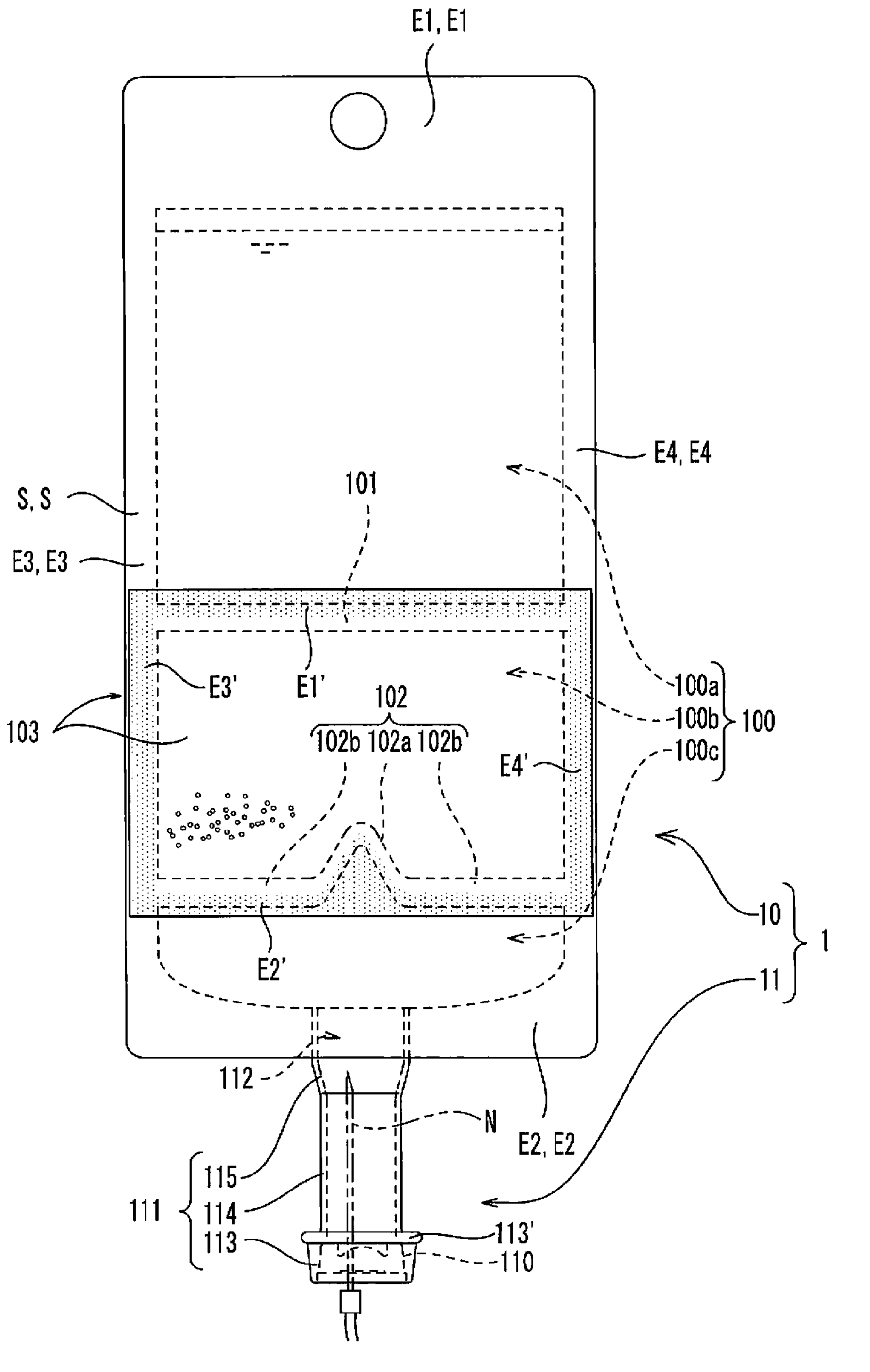
FIG. 1 is a front view of an entire infusion solution bag according to a first embodiment of the present invention.
Figure 2:
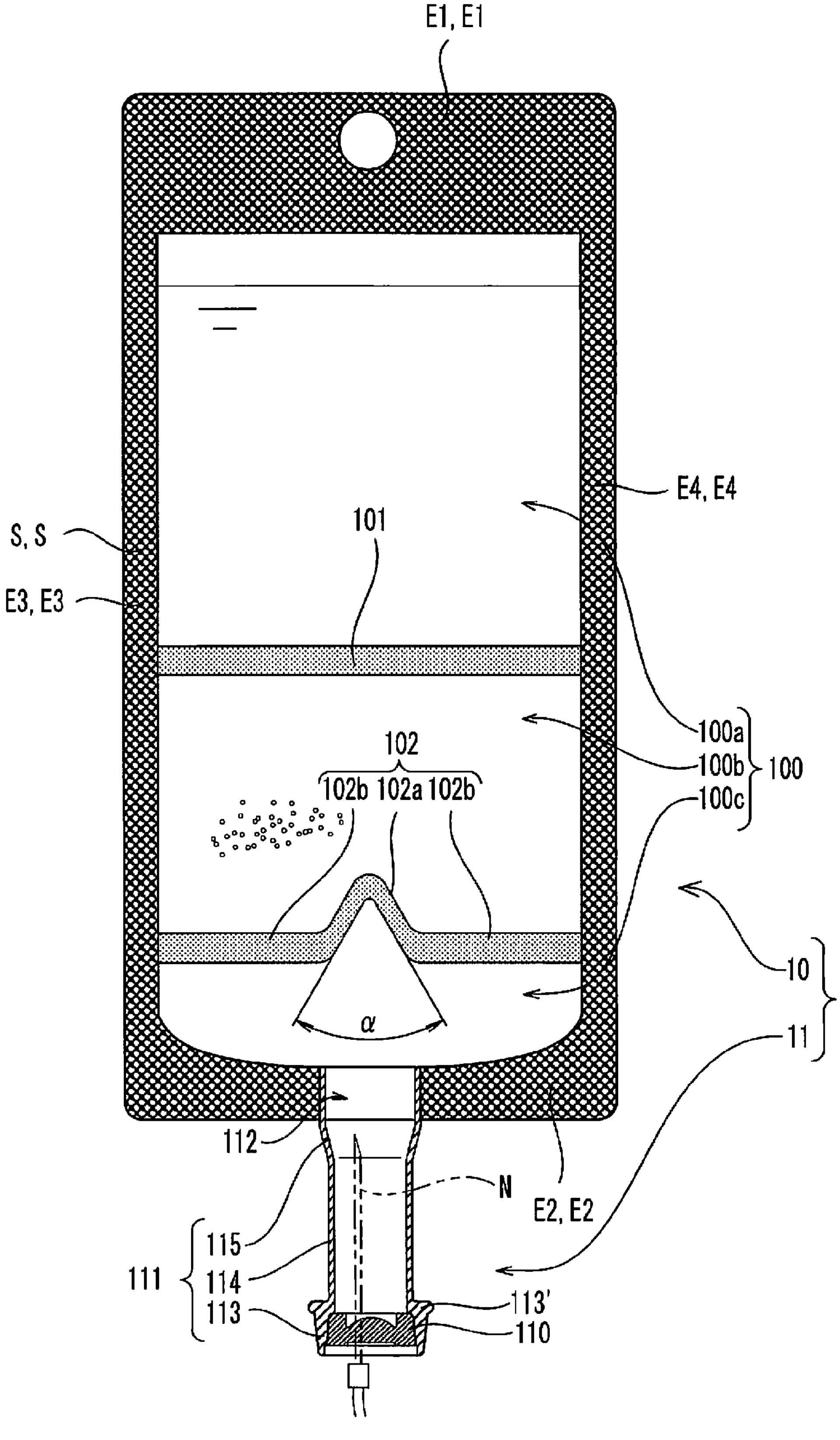
FIG. 2 is a vertical cross sectional view of the infusion solution bag of the first embodiment with sealed portions hatched.

As shown in FIGS. 1 and 2, an infusion solution bag 1 of this embodiment includes a bag body 10 having an inner space 100 for accommodation of at least a medicine, and a port member (port member for the infusion solution bag) 11 fluidly connected to the bag body 10.

The bag body 10 is formed by overlapping resin sheets S, S and sealing end portions E1, E1, E2, E2, E3, E3, E4 and E4 together, and the inner space 100 designed to be able to accommodate at least a medicine within an area surrounded by the sealed portions. The bag body 10 of this embodiment is formed by sealing the outer peripheral end portions E1, E1, E2, E2, E3, E3, E4 and E4 together along the entire peripheries of the two resin sheets S, S. Various types of resin sheet may be used as the resin sheets S, S of the bag body 10, and in this embodiment, synthetic resin sheet of polypropylene (PP) and polyethylene (PE) is employed in consideration of the sealability between the resin sheets S, S or sealability relative to the port member 11.

The inner space 100 of the bag body 10 of this embodiment is divided into three sections, respectively defining a space (hereinafter referred as a first chamber) 100*a* for accommodation of a dilution solution, a space (hereinafter referred as a second chamber) 100*b* for accommodation of a medicine (a powdered medicine in this embodiment), and an unoccupied space (hereinafter referred as a third chamber) 100*c*. Specifically, the bag body 10 of this embodiment has a vertically elongated shape, and the inner space 100 thereof is divided into three sections by forming two weak seal portions 101, 102, which extend in a lateral direction of the bag body 10 (a direction orthogonal to the longitudinal direction) and are spaced apart from each other, and the first chamber 100*a*, the second chamber 100*b* and the third chamber 100*c* are formed in this order from one end to the other end in the longitudinal direction of the bag body 10.

The weak seal portions 101, 102 are formed to have bonding power (adhesive power) between the resin sheets S, S weaker than the bonding power (adhesive power) between the outer peripheral end portions E1, E1, E2, E2, E3, E3, E4 and E4 of the two resin sheets S, S so that these portions are precedently peeled off away from each other. In the following description, the weak seal portion 101 separating the first chamber 100*a* and the second chamber 100*b* from each other is referred as a first weak seal portion, and the weak seal portion 102 separating the second chamber 100*b* and the third chamber from each other is referred as a second weak seal portion.

The first weak seal portion 101 is formed into a band shape extending straight in the lateral direction of the bag body 10. On the other hand, the second weak seal portion 102 includes an easy-to-open portion 102*a* projecting towards the second chamber 100*b*, and straight portions 102*b*, 102*b* continued from the easy-to-open portion 102*a* and extending from the opposite sides of the easy-to-open portion 102*a* substantially straight.

The easy-to-open portion 102*a* is formed as projecting in a V-shape with an apex located on the side of the second chamber 100*b*. That is, the easy-to-open portion 102*a* is formed by a bent area (V-shaped area) of an end edge on the side of the third chamber 100*c*, the end edge having an apex so as to convexly project towards the second chamber 102*a* while being concavely oriented towards the third chamber 100*c*. When the easy-to-open portion 102*a* is formed to project in the V-shape (chevron shape), an apex angle $\alpha$ of the easy-to-open portion 102*a* is preferably in the range of 20 degrees to 150 degrees. According to the second weak seal portion 102 having the above arrangement, the easy-to-open portion 102*a* starts rupturing precedently, as a result of the concentration of the force generated by pressing the infusion solution bag 1 to the easy-to-open portion 102*a*, and thus opens earlier than the residual portions (straight portions 102*b*, 102*b*).

In the infusion solution bag 1 of this embodiment, film materials having gas barrier property for preventing passing of gasses or moisture (hereinafter referred as gas-barrier films) 103, 103 are attached to the bag body 10 (resin sheets S, S so as to cover an area defining the second chamber 100*b*.

For the gas barrier films 103, 103, it is possible to employ, for example, a film having a multi-layer structure, in which a layer formed by vapor depositing silica and/or alumina on polyethylene terephthalate (PET), or a layer formed by attaching aluminium foil to PET, is bonded to a layer of olefin resin such as polyethylene (PE).

The gas barrier films 103, 103 respectively have opposite end portions E1', E2' overlapped respectively to the first weak seal portion 101 and the second weak seal portion 102, and opposite lateral side end portions E3', E4' overlapped respectively to end portions E3, E4 (parts of the outer peripheral end portion) of the short side direction of the resin sheets S, S, and with this state, are respectively bonded to the outer surfaces of the two resin sheets S, S of the bag body 10.

More specifically, one end portions (close to the first chamber 100*a*) E1' of the gas barrier films 103, 103 extend through the substantially entire length of the bag body 10 in the lateral direction, and are at least partly overlapped and sealed to the first weak seal portion 101. On the other hand, the opposite end portions (close to the third chamber 100*c*) E2' of the gas barrier films 103, 103 extend through the substantially entire length of the bag body 10 in the lateral direction, and are overlapped and sealed to the second weak seal portion 102 on the side of the third chamber 100*c* (on the discharge side).

In the thus structured infusion solution bag 1, the gas barrier films 103, 103, 103 are bonded to the bag body 10 while being overlapped to the first weak seal portion 101 and the second weak seal portion 102, and thus the bonded portions E1', E2' are reinforced. As described above, the easy-to-open portion 102*a* is formed to project towards the second chamber 100*b* so that the second weak seal portion 102 is entirely and easily ruptured and opened, that is, the second chamber 100*b* is brought into communication with the third chamber 100*c*, due to the rupture (opening) of the easy-to-open portion when in opening (when the infusion solution bag 1 has been pressed).

Figures 3A, 3B, 3C, 3D:
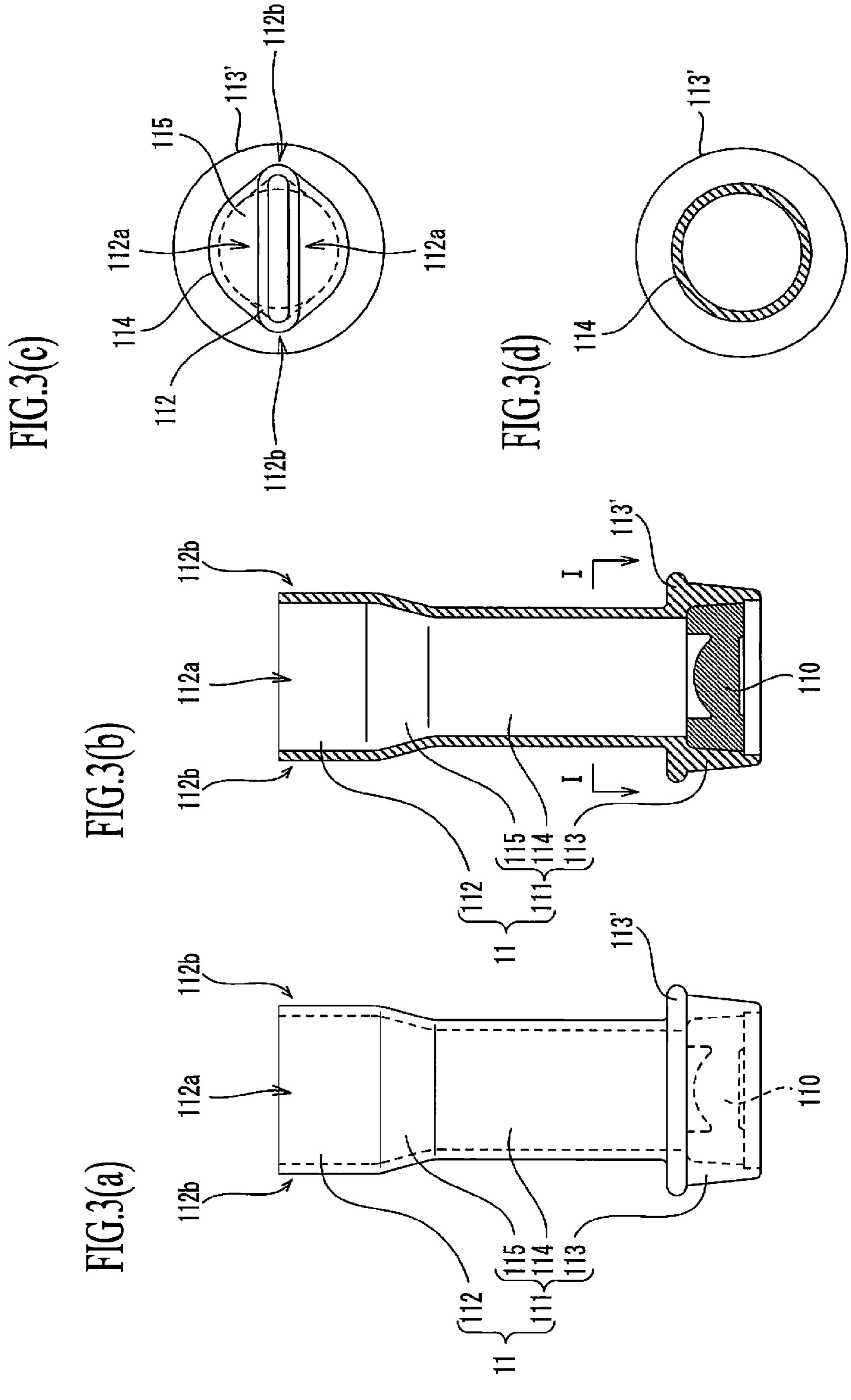
FIGS. 3(*a*) to 3(*d*) show a port member of the first embodiment, in which FIG. 3(*a*) is a front view, FIG. 3(*b*) is a vertical cross sectional view, FIG. 3(*c*) is a plan view and FIG. 3(*d*) is a cross sectional view taken along a line I-I in FIG. 3(*b*).

As shown in FIGS. 3(*a*) to 3(*d*), the port member 11 includes a tubular body portion 111 that has one end (a to-be-plugged portion 113 hereinafter referred) plugged by a plug member 110 structured to enable a hollow needle N to be pierced thereinto, and a to-be-sealed portion 112 having a flattened tubular shape continuously formed with the other end of the body portion 111 and having an inner space communicated with the inside of the body portion 111.

The body portion 111 and the to-be-sealed portion 112 are formed by an integrally formed resin molded product, and in this embodiment, they are molded with a polyolefin resin, such as polypropylene (PP) in this embodiment. The body portion 111 of this embodiment is integrally formed with the plug member 110 by double molding.

The body portion 111 of this embodiment includes a to-be-plugged portion 113 having a cylindrical tube shape plugged by the plug member 110, a connection tube portion 114 having a cylindrical tube shape continuously formed with the to-be-plugged portion 113 and having an inner space communicated with the inside of the to-be-plugged portion 113, and a deformed tube portion 115 for connection between the connection tube portion 114 and the to-be-sealed portion 112. The to-be-plugged portion 113 is larger in diameter than the connection tube portion 114, and the to-be-plugged portion 113 and the connection tube portion 114 together define a substantially stepped rod shaped appearance.

The to-be-plugged portion 113 constitutes one end of the body portion 111 in the axial direction, and has an inner diameter larger than the inner diameter of the connection tube portion 114. The to-be-plugged portion 113 and the connection tube portion 114 are continuously formed to have a stepped inner hole of the body portion 111.

The to-be-plugged portion 113 of this embodiment has a flange portion 113' extending radially outwardly from one end (end to which the connection tube portion 114 is connected) of the to-be-plugged portion 113. The flange portion 113' is designed to suspend an infusion solution bag 1 therethrough by a rail (not shown) when it is supplied during manufacturing. Therefore, the flange portion 113' is not an essential component, and may be appropriately provided according to the arrangement of the manufacturing facility.

The length (preferably the total length of the to-be-plugged portion 113 and the connection tube portion 114) from one end to the other end of the body portion 111 of the port member 11 of this embodiment is set to be longer than the hollow needle N to be pierced into the plug body 110. That is, the port member 11 has such a length as not to allow the leading end of the hollow needle N, which has been pierced into the plug body 110, to reach an area where the bag body exists, so that the hollow needle N is prevented from being erroneously pierced into the bag body 10.

The deformed tube portion 115 provides connection between the connection tube portion 114 having a cylindrical tube shape and the to-be-sealed portion 112 having a flattened tube shape in communication with each other, and is deformed from the cylindrical tube shape to the flattened tube shape as it advances from one end to the other end. Accordingly, while the deformed tube portion 115 has one opening having a substantially rounded shape, to which the connection tube portion 114 is connected, and an other opening having a flattened shape corresponding to the to-be-sealed portion 112, to which the to-be-sealed portion 112 is connected.

The to-be-sealed portion 112 of this embodiment is formed into a radially flattened tube shape, as shown in FIG. 3(*c*). Whereby, the to-be-sealed portion 112 has curved surfaces having large curvature radius or portions 112*a*, 112*a* shaped into substantially flat surface, and portions 112*b*, 112*b* having very small curvature radius, in the circumferential direction. That is, the to-be-sealed portion 112 is formed to have a major axis (between the portions 112*b*, 112*b* having small curvature radius) and a minor axis (between the curved surfaces having large curvature radius or portions 112*a*, 112*a* shaped into substantially flat surface). The to-be-sealed portion 112 of this embodiment is formed to have a minor axis smaller than the diameter of the connection tube portion 114 and a major axis larger than the diameter of the connection tube portion 114, on the premise that a medicine can pass therethrough. More specifically, the to-be-sealed portion 112 is formed to have a minor axis of the inner diameter being 5% to 50% of the inner diameter (diameter) of the connection tube portion 114, and a major axis of the inner diameter being 110% to 150% of the inner diameter (diameter) of the connection tube portion 114. Taking into account the passing of a medicine, the opening area of the to-be-sealed portion 112 is preferably in a range of 20% to 40% relative to the opening area of the connection tube portion 114.

Figure 4B:
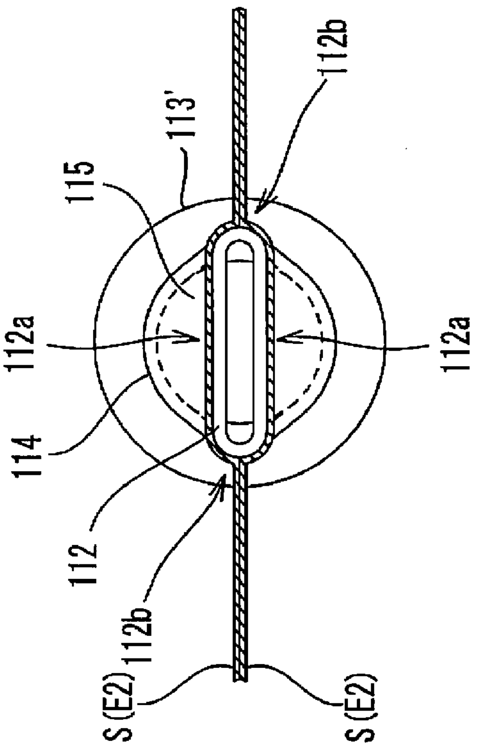
FIGS. 4(*a*) and (*b*) show the port member of the first embodiment when it is fluid tightly connected to a bag body, in which FIG. 4(*a*) shows a state in which a to-be-sealed portion is held between end portions of resin sheets, and FIG. 4(*b*) shows a state in which the to-be-sealed portion is sealed to the overlapped resin sheets.
Figure 4A:
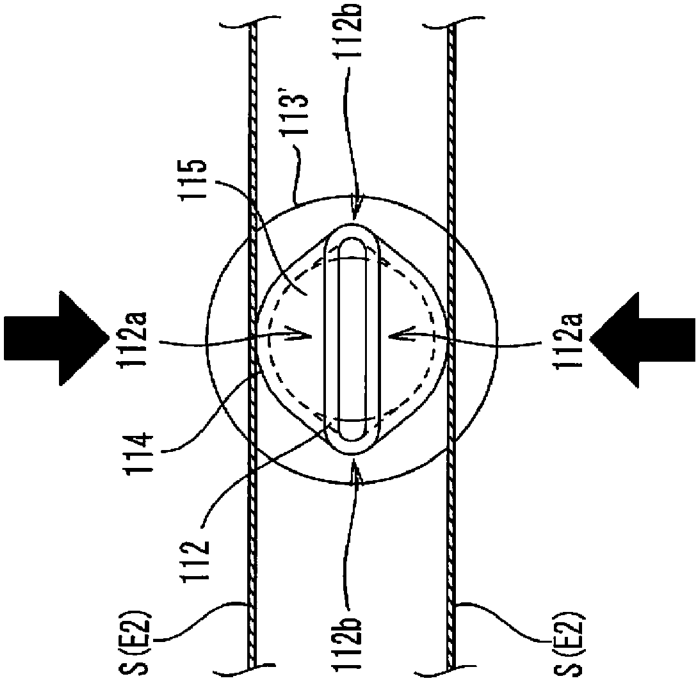

The thus structured port member 11 is held between end portions E2, E2 of two resin sheets S, S (end portions E2, E2 of the overlapped resin sheets S, S), which together form the bag body 10, from the other sides in the direction of a minor axis of the to-be-sealed portion 112, as shown in FIG. 4(*a*), and with this position, the end portions E2, E2 of the respective resin sheets S, S are sealed to the to-be-sealed portion 112, as shown in FIG. 4(*b*). The port member 11 of this embodiment is held between the end portions E2, E2 of the resin sheets S, S, which are the other ends in the longitudinal direction of the bag body 10, that is, the end portions E2, E2 defining the third chamber 100*c*, and with this position, the port member 11 is sealed to the end portions E2, E2, so that the port member is fluid tightly connected to the bag body 10 with the inside of the port member 11 communicated to the inside of the third chamber 100*c* as an unoccupied chamber (cf. FIGS. 1 and 2).

Accordingly, the end portions E2, E2 of the resin sheets S, S sealed to the to-be-sealed portion 112 are shaped to conform to portions having large curvature radius in the circumferential direction of the to-be-sealed portion 112 (or portions extending straight) 112*a*, 112*a*, and the infusion solution bag 1 has a shape approximate to a substantially flat shape throughout the entire length of the end portions E2, E2 of the resin sheets S, S, in which the portions thereof sealed to the to-be-sealed portion 112 are continued with the portions having the end portions E2, E2 of the resin sheets S, S sealed together. Consequently, it is possible to suppress occurrence of gaps or wrinkles along boundaries between the sealed portions of the end portions E2, E2 of the resin sheets S, S, and the sealed portion of the end portions E2, E2 of the resin sheets S, S and the to-be-sealed portion 112.

Figures 5A, 5B, 5C, 5D, 5E, 5F:
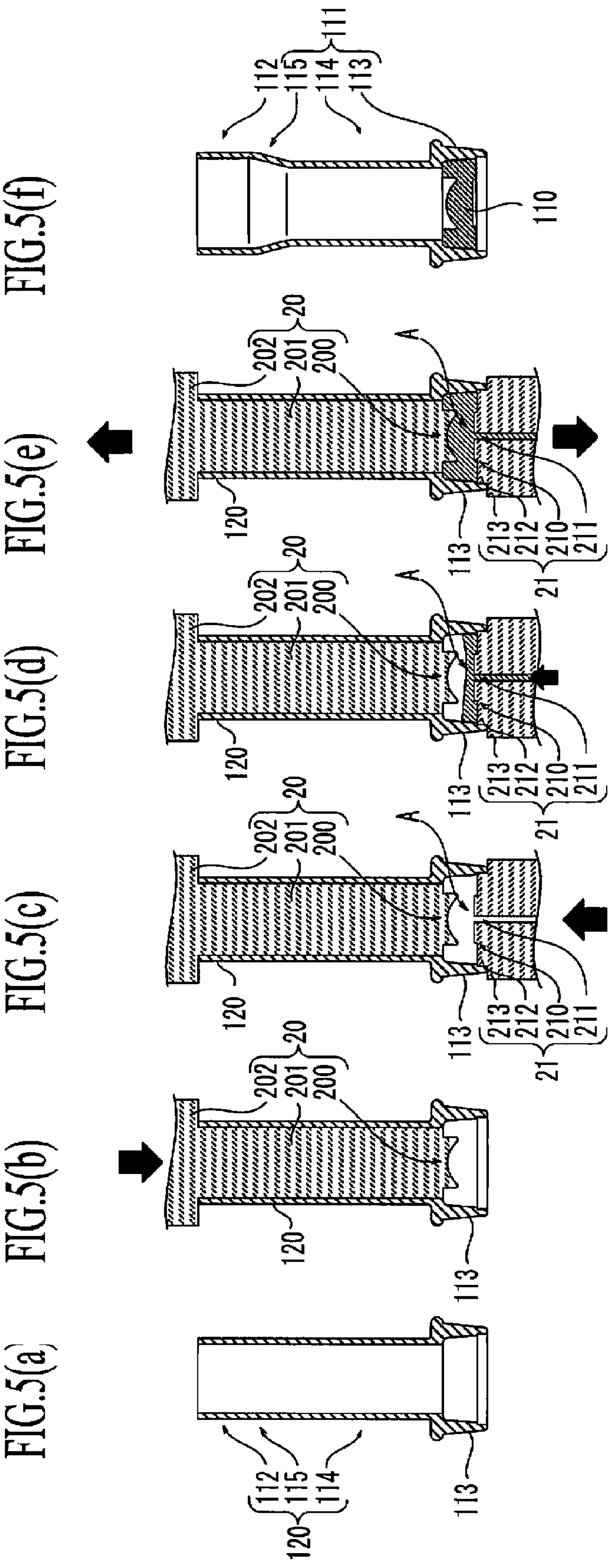
FIGS. 5(*a*) to 5(*f*) are explanatory views for explaining a manufacturing method of the port member of the first embodiment, in which FIG. 5(*a*) is a vertical cross sectional view of a molded product having a connection tube portion, a deformed tube portion and a to-be-sealed portion, all of which together form a tubular member having a cylindrical tube shape, FIG. 5(*b*) shows a state in which a first molding die has been inserted into a tube body, FIG. 5(*c*) shows a state in which a second molding die has been inserted into a to-be-plugged portion with the first molding die placed in the tube body, FIG. 5(*d*) shows a state in which a molding material is injected, FIG. 5(*e*) shows a state in which the filled molding material has been cured, and the first and second molding dies are pulled out, and FIG. 5(*f*) shows a state in which the to-be-sealed portion has been molded into a flat shape.

Now, the description will be made for the method of forming of the port member 11 having the above structure. First, as shown in FIG. 5(*a*), a molded product is formed, in which the to-be-plugged portion 113 and the connection tube portion 114 have the above forms, and the deformed tube portion 115 and the to-be-sealed portion 112 are continued with the connection tube portion 114 to have a cylindrical tube shape. This molded product has the to-be-sealed portion 112, the deformed tube portion 115 and the connection tube portion which are integrally provided to form a tubular body 120 having a substantially uniform diameter throughout the entire length. As shown in FIG. 5(*b*), a first molding die 20 is inserted into the tubular body 120 through a portion which is to be molded into the to-be-sealed portion. The first molding die 20 has at a leading end a molding projection 200 for forming the inner surface of the plug member 110, and includes a rod portion 201 to be inserted into the tube body 120 with the inner surface of the tube body 120 slidingly contacting the outer surface of the rod portion 201, and a stopper portion 202 continuously formed with a proximal end of the rod portion 201 for stopping the further insertion of the rod portion 201 by coming into contact with an opening end edge of the tube body 120 when the molding projection 200 has reached a position at which the inner surface of the plug member 110 is formed.

Then, as shown in FIG. 5(*c*), the second molding die 21 is fitted into an opening end portion of the to-be-plugged portion 113. The second molding die 21 has at a leading end a molding projection 210 for forming an outer surface of the plug member 110 and an outlet port 211 for discharging a molding material for forming the plug member 110 towards the molding projection 210, and includes a fit-in portion 212 to be fittingly engaged with the to-be-plugged portion 113 through an opening end of the to-be-plugged portion 113, and a stopper portion 213 continuously formed with a proximal end of the fit-in portion 212 for stopping the further insertion of the fit-in portion 212 by coming into contact with an opening end edge of the to-be-plugged portion 113 when the molding projection 210 has reached a position at which the outer surface of the plug member 110 is formed. In this embodiment, the insertion of the first molding die 20 into the tube body 120 is made prior to the fitting engagement of the second molding die 21 into the to-be-plugged portion 113. However, the fitting engagement of the second molding die 21 may be made prior to the insertion of the first molding die 20, or the insertion of the first molding die 20 and the fitting engagement of the second molding die 21 may be simultaneously made.

Then, as shown in FIG. 5(*d*), with the first molding die 20 (rod portion 201) inserted into the tube body 120 and the second molding die 21 (fit-in portion 212) fittingly engaged with the to-be-plugged portion 113, a molding material is discharged through the outlet port 211 and filled in a space A surrounded by the to-be-plugged portion 113, the first molding die 20 (molding projection 200) and the second molding die 21 (molding projection 210). The molding material has fluidity at an initial stage and then is cured with time to exhibit elasticity. An example of the molding material includes a thermoplastic elastomer (a polyolefin elastomer such as a polypropylene elastomer, or a mixture of a styrene elastomer and a polyolefin elastomer). Then, as shown in FIG. 5(*e*), after curing of the filled molding material, the first molding die 20 and the second molding die 21 are pulled out, thereby forming a molded product in which the to-be-plugged portion 113 is held plugged with the plug member 110. After that, a portion of the molded product corresponding to the to-be-sealed portion 112 of the tube body 120 is radially pressed (preferably heat pressed), thereby forming the to-be-sealed portion 112 into a radially flattened shape, as shown in FIG. 5(*f*). Thus, the forming of the port member 11 is finished.

As described above, when the bag body 10 is formed by the two resin sheets S, S, the to-be-sealed portion 112 is held between the end portions E2, E2 of the two resin sheets S, S (the end portions E2, E2 of the overlapped resin sheets S, S) from the opposite sides in the direction of a minor axis of the to-be-sealed portion 112, and with this position, the end portions E2, E2 of the respective resin sheets S, S are sealed to the to-be-sealed portion 112, so that the port member 11 is fluid tightly connected to the bag body 10 to be held in fluid communication with the same (cf. FIGS. 1, 2 and 4).

The infusion solution bag 1 provided with the thus structured port member 11, in which a medicine and a dilution solution are accommodated, is stored and transported. At this time, the bag body 10 is sometimes folded into two in the longitudinal direction. Since the infusion solution bag 1 of this embodiment has the to-be-sealed portion 112 of the port member 11 formed into a flattened tube shape, partial contacts between a portion of the port member 11 corresponding in position to the to-be-sealed portion 112 and a portion of the resin sheets S, S, corresponding in position to that portion can be reduced, with the result that the resin sheets S, S are suppressed from being ruptured.

As described above, the infusion solution bag 1 and the port member 11 for it, of this embodiment has the to-be-sealed portion 112 formed into a radially flattened shape, which is to be held between and sealed to the end portions E2, E2 of the resin sheets S, S. Therefore, it is possible to prevent occurrence of gaps or wrinkles in a sealed portion during manufacturing process, and hence prevent the resin sheets S, S of the bag body 10 from being damaged during storage or transportation.

Figure 6:
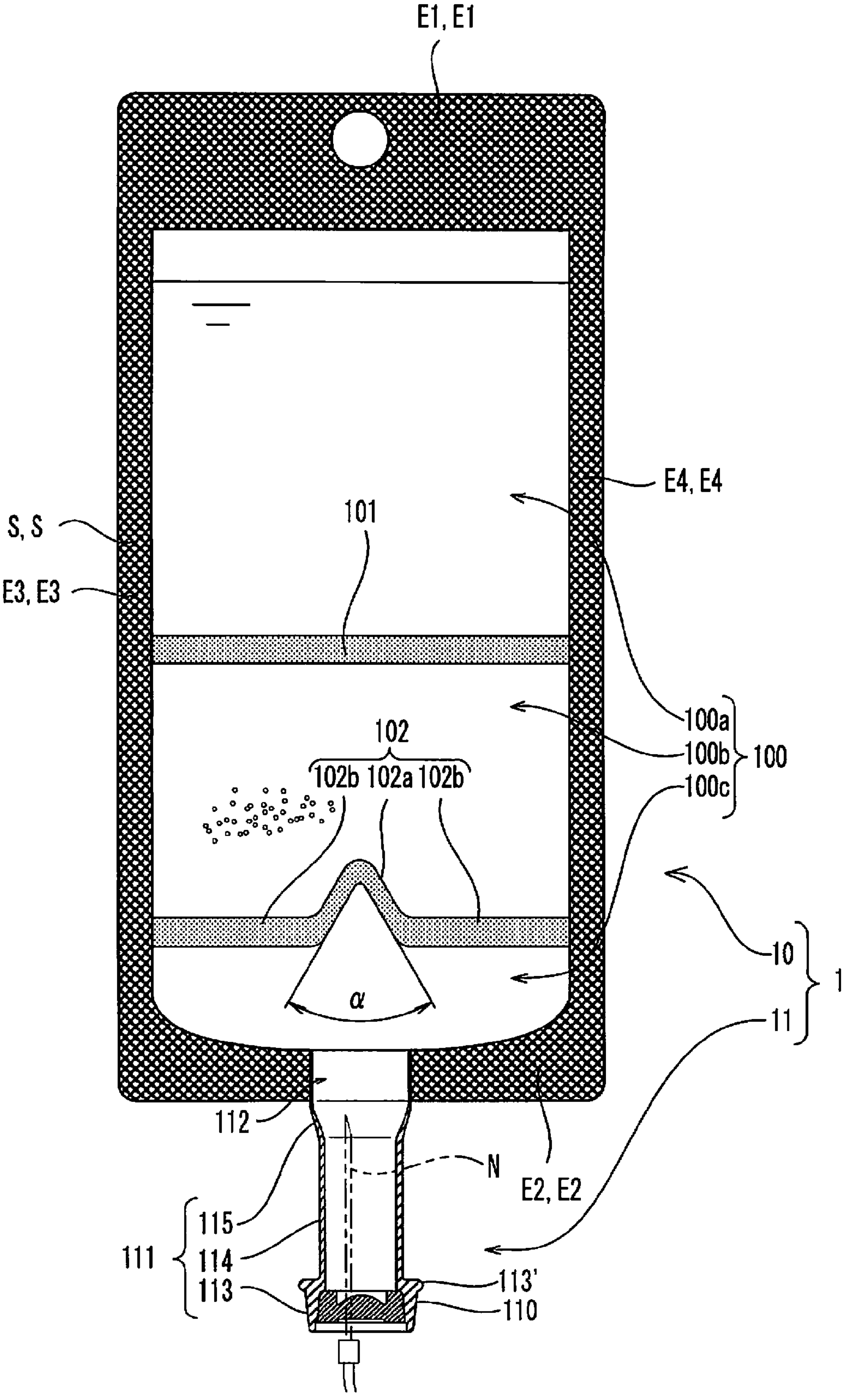
FIG. 6 is a vertical cross sectional view of an infusion solution bag according to a second embodiment of the present invention with sealed portions hatched.

Now, the description will be made for a second embodiment of the present invention. As shown in FIG. 6, an infusion solution bag of this embodiment has the same structure as the infusion solution bag 1 of the first embodiment except for the structure of the to-be-sealed portion of the port member 11. Thus, the following description will be made in detail for the to-be-sealed portion of the port member and a deformed tube portion, which relates to the to-be-sealed portion, while omitting the description for the bag body by allocating the same names and the same reference characters thereto. For the port member, the same names and the same reference characters are allocated to the elements or members corresponding to those of the first embodiment.

Figures 7A, 7B, 7C:
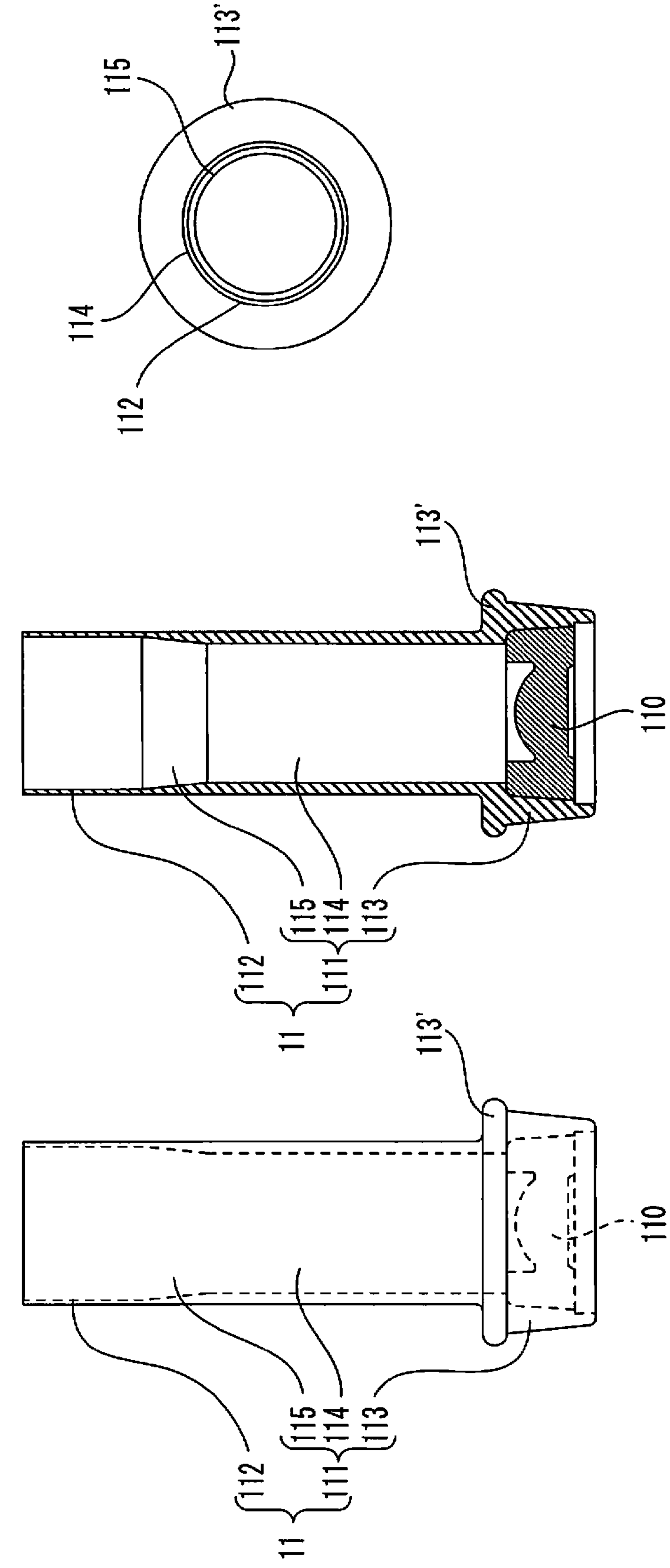
FIGS. 7(*a*) to 7(*c*) show a port member of the second embodiment, in which FIG. 7(*a*) is a front view, FIG. 7(*b*) is a vertical cross sectional view and FIG. 7(*c*) is a plan view.

The port member 11 of this embodiment has, as shown in FIGS. 7(*a*) to 7(*c*), the deformed tube portion 115 and the to-be-sealed portion 112 which are formed into a cylindrical tube shape and are structured to be radially deformable. In the port member 11 of this embodiment, the connection tube portion 114, the deformed tube portion 115 and the to-be-sealed portion 112 have the same outer diameter. On the other hand, the inner diameter of the to-be-sealed portion 112 is larger than the inner diameter of the connection tube portion 114, and the deformed tube portion 115 is set to be increased in inner diameter from the side of the connection tube portion 114 towards the side of the to-be-sealed portion 112, thereby having an inner diameter gradually increased from the inner diameter of the connection tube portion 114 to the inner diameter of the to-be-sealed portion 112. Whereby, the port member 11 of this embodiment is so formed to have the thickness of the to-be-sealed portion 112 thinner than the connection tube portion 114 and the deformed tube portion 115 close to the connection tube portion 114 thicker than the deformed tube portion 115 close to the to-be-sealed portion 112. In this embodiment, since the deformed tube portion 115 is also partially thinned, the total length of the to-be-plugged portion 113 and the connection tube portion 114 is set to be longer than the length of the hollow needle N so as to prevent the leading end of the hollow needle N, which has been pierced through the plug member 110, from reaching a thinned portion of the deformed tube portion 115.

The port member 11 of this embodiment is formed with the thinned to-be-sealed portion 112, as described above, and therefore is deformed into a radially flattened shape by pressing the to-be-sealed portion 112 in the radial direction. The to-be-sealed portion 112 of this embodiment has the same outer diameter as that of the connection tube portion 114, and therefore is structured to have a minor axis smaller than the diameter (outer diameter) of the connection tube portion 114, and a major axis larger than the diameter (outer diameter) of the connection tube portion 114. More specifically, the thickness of the to-be-sealed portion 112 is determined so that the to-be-sealed portion 112 in a deformed state (in a radially flattened state) has a minor axis of the inner diameter being 5% to 50% of the inner diameter (diameter) of the connection tube portion 114, and a major axis of the inner diameter being 110% to 150% of the inner diameter (diameter) of the connection tube portion 114. The to-be-sealed portion 112 of the port member 11 of this embodiment is deformed into a flattened shape by pressing in the radial direction, but ensures an opening for allowing passage of a medicine due to the self-restoration force.

Figure 8B:
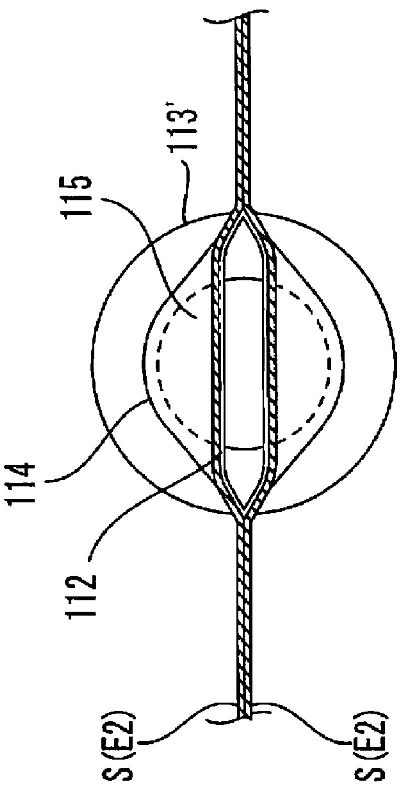
FIGS. 8(*a*) and (*b*) show the port member of the second embodiment when it is fluid tightly connected to a bag body, in which FIG. 8(*a*) shows a state in which a to-be-sealed portion is held between end portions of resin sheets, and FIG. 4(*b*) shows a state in which the to-be-sealed portion has been sealed to the overlapped resin sheets.
Figure 8A:
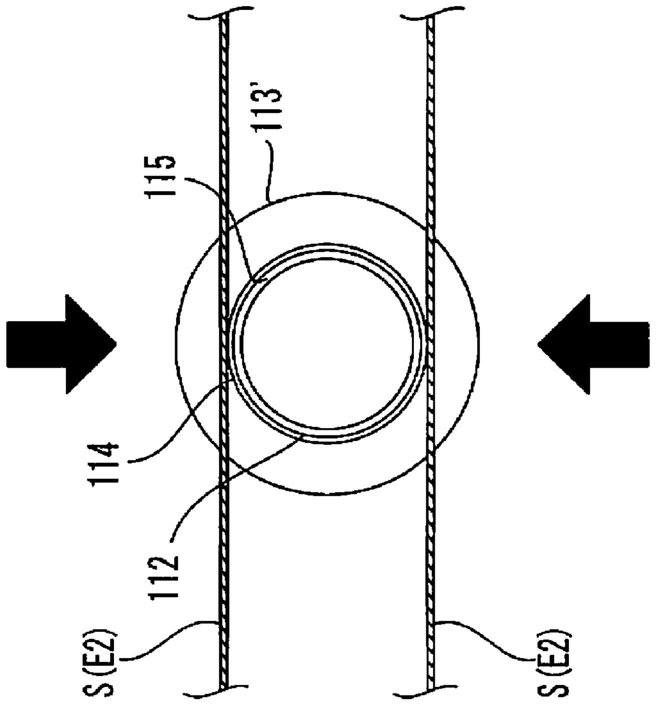

According to the infusion solution bag 1 of this embodiment, in the same manner as the first embodiment, the to-be-sealed portion 112 is sealed to the end portions E2, E2 of the respective resin sheets S, S while being held between the end portions E2, E2 of the resin sheets (end portions E2, E2 of the overlapped resin sheets S, S) of the bag body 10 from the opposite sides of the to-be-sealed portion 112, as shown in FIG. 8(*a*), when the end portions E2, E2 of the overlapped resin sheets S, S are sealed together in order to form the bag body 10. At this moment, as shown in FIG. 8(*b*), the resin sheets S, S are sealed to the to-be-sealed portion 112 held flattened by pressing force for sealing the resin sheets S, S, and the to-be-sealed portion 112 is fluid tightly connected to the bag body 10 with the inside of the third chamber 100*c* as the unoccupied chamber communicated with the inside of the port member 11 (cf. FIG. 6). The deformed tube portion 115 closer to the connection tube portion 114 has a cylindrical tube shape and close to the to-be-sealed portion 112 is deformed into a flattened tube shape, as the to-be-sealed portion 112 is flattened, as described above.

According to the infusion solution bag 1 of this embodiment, as well, the end portions E2, E2 of the resin sheets S, S sealed to the to-be-sealed portion 112 are held to conform to a portion of the to-be-sealed portion having large curvature radius in the circumferential direction (or portions extending straight), in the same manner as the first embodiment. Thus, a portion of the resin sheets S, S sealed to the to-be-sealed portion is continued with portions where the end portions E2, E2 of the resin sheets S, S so that the end portions E2, E2 of the resin sheets S, S are held substantially flattened throughout the entire length. Consequently, it is possible to suppress occurrence of gaps or wrinkles along boundaries between portions at which the end portions E2, E2 of the resin sheets S, S are sealed together, and a portion at which the end portions E2, E2 of the resin sheets S, S and the to-be-sealed portion 112 are sealed together.

The infusion solution bag 1 of this embodiment is also folded into two in the longitudinal direction during storage or transportation. Since the to-be-sealed portion 112 of the port member 11 is held flattened and thin, it is possible to reduce partial contact between the portion of the port member 11 corresponding in position to the to-be-sealed portion 112, and the resin sheets S, S corresponding in position to that portion, and hence suppress rupture of the resin sheets S, S.

As described above, according to the infusion solution bag 1 of this embodiment, the to-be-sealed portion 112 of the port member 11 is held flattened by sealing the resin sheets S, S of the bag body 10 together, and therefore it is possible to produce the same functions and effects as those of the first embodiment. According to the port member 10 of this embodiment, the to-be-sealed portion 112 is formed with a thin wall and therefore is able to be flattened when it is sealed to the bag body 10 (resin sheets S, S). Thus, it is possible to omit the step of previously forming the to-be-sealed portion 112 into a flattened shape before forming the port member 11, and realize low cost manufacturing.

The present invention is not necessarily to limited to any one of the aforesaid embodiments, and can be subjected to various modifications within the intended scope of the present invention.

In the first and second embodiments, as double molding for integrally forming the body portion 111 and the plug member 110 with different materials, a molding material is filled in a previously molded body portion 111 and then cured to integrally mold the plug member 110 with the body portion 111. The double molding is not necessarily limited to this. For example, it is possible to employ double molding, in which the plug member 110 is previously molded, then the plug member 110 is placed within a die for molding the body portion 111, and a molding material is filled between the plug member 110 and the die, and cured to integrally mold the body portion 111 with the plug member 110.

In the first and second embodiments, the plug member 110 is integrally molded with the to-be-plugged portion 113, but the present invention is not necessarily limited to this. For example, a previously molded plug member 110 may be fittingly engaged with the to-be-plugged portion 113. That is, during distribution, one end of the body portion 111 of the port member 11 is not necessarily plugged by the plug member 110, and a molded product with the to-be-plugged portion 113, the connection tube portion 114, the deformed tube portion 115 and the flattened tube shaped to-be-sealed portion 112 of the port member 11 integrally formed may be independently distributed as a port member for an infusion solution bag. In a case where the plug member 110 is independently formed, it is not necessary to insert the first molding die 20 for molding the plug member 110 into the tube body 120, and therefore the to-be-sealed portion 112 of the port member 11 of the first embodiment may be formed into a flattened shape before or after the fitting engagement of the plug member 110. However, in order to increase integrity, that is, plugging performance between the to-be-plugged portion 113 and the plug member 110, integral molding is preferable as in the aforesaid embodiments.

In the first and second embodiments, the bag body 10 is formed by overlapping two resin sheets S, S and sealing their end portions E1, E1, E2, E2, E3, E3, E4 and E4 to each other. However, the present invention is not necessarily limited to this. For example, the bag body 10 may be formed by folding a single resin sheet into two, and having two areas facing each other (overlapped each other) around the folding ridge sealed together along their end portions, or having two areas sealed along the entire peripheral end portions of the two areas.

Figure 9A:
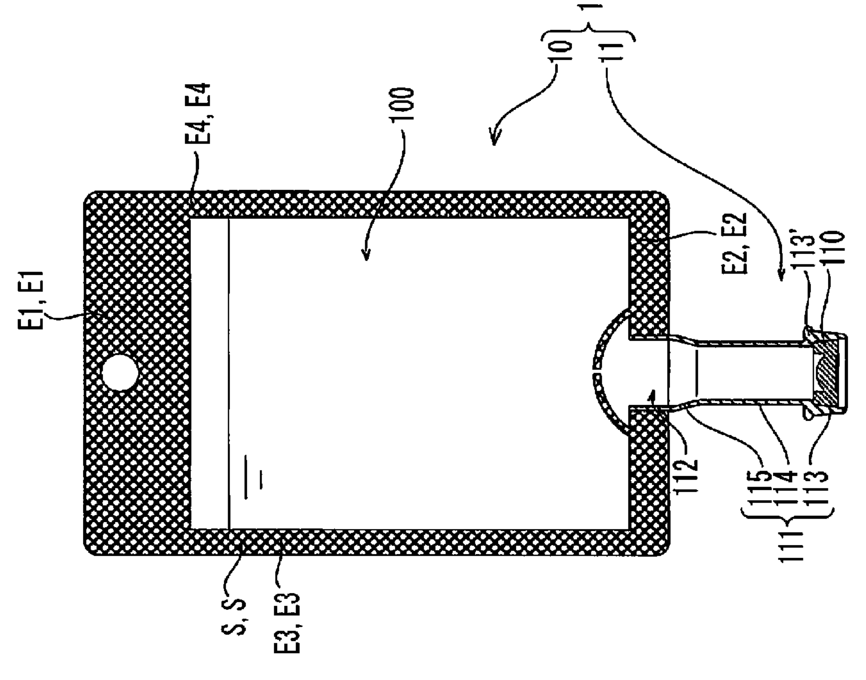
FIGS. 9(*a*) and 9(*b*) show another embodiment of the present invention, in which FIG. 9(*a*) is a cross sectional view of an infusion solution bag having a bag body with an inner space not divided, and FIG. 9(*b*) is a cross sectional view of an infusion solution bag having an inner space divided into two sections.
Figure 9B:
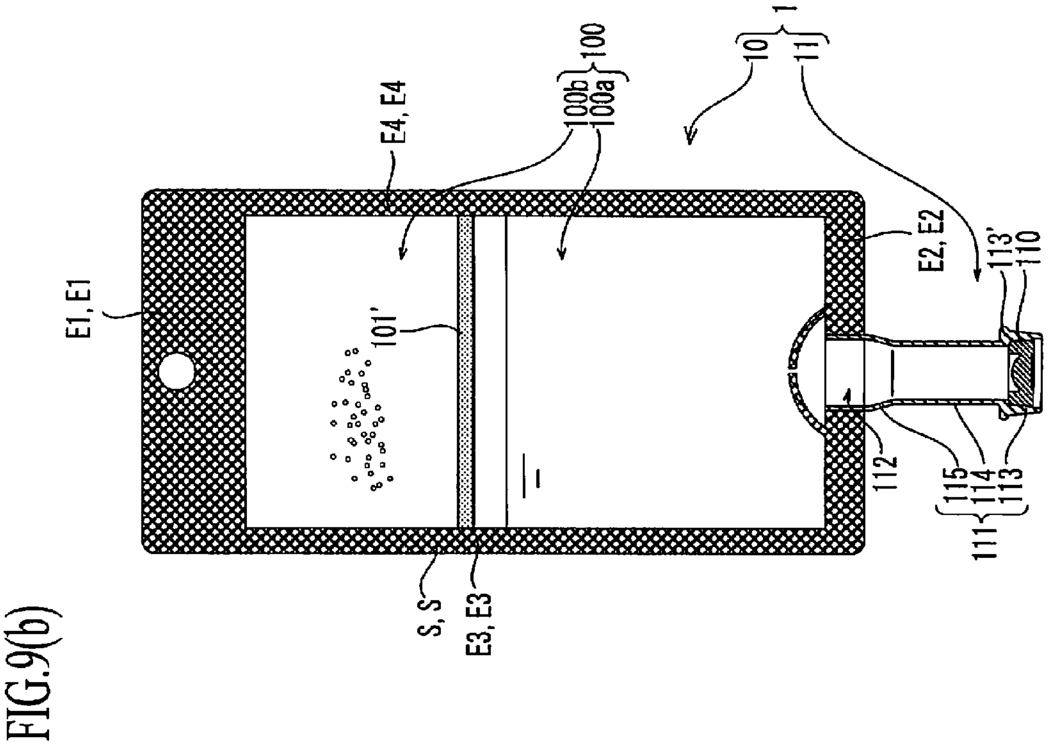

In the first and second embodiments, the description was made for the infusion solution bag 1 with the inner space 100 of the bag body 10 divided into three sections. However, the present invention is not necessarily limited to this. For example, it is possible to employ an arrangement, in which only an inner space 100 for accommodation of a medicine (medicinal solution) is formed in the bag body 10, as shown in FIG. 9(*a*), or an inner space 100 of the bag body 10 is divided into two sections by a weak seal portion 101' to form a first chamber 100*a* for accommodation of a dilution solution and a second chamber 100*b* for accommodation of a medicine, as shown in FIG. 9(*b*). That is, any types of the bag body 10 provided with the port member 11 may be employed, provided that they form the inner space 100 for accommodation of at least a medicine.

In the first and second embodiments, a powder medicine is accommodated within the inner space 100 (second chamber 100*b*). However, a medicine to be accommodated within the bag body 10 may be liquid. As described above, when the inner space 100 is designed to accommodate only a medicine, it is a matter of course that only a liquid medicine is employed. In the aforesaid embodiments, the description was made for the infusion solution bag 1 with a medicine and a dilution solution separated from each other. In this regard, when a medicine is liquid, the medicine contains a diluting solution as a component thereof. Therefore, it is a matter of course that the infusion solution bag 1 with the port member 11 mounted thereto may be designed to accommodate only a dilution solution as a medicine.

In the first and second embodiments, the body portion 111 (the to-be-plugged portion 113 and the connection tube portion 114) is set to be longer than the length of the hollow needle N. However, the present invention is not necessarily limited to this. For example, the enter length of the port member 11 may be set to be longer than the length of the hollow needle N to prevent the leading end of the hollow needle N, which has been pierced through the plug member 110, from reaching the bag body 10. That is, the length of the port member 11 may be set so as not to allow the hollow needle N, which has been pierced through the plug member 110, to be pierced through the bag body 10. However, as described above, the deformed tube portion 115 is a portion changing in shape from a cylindrical tube shape to a flattened tube shape with an inner portion decreasing in space towards the to-be-sealed portion 112. Therefore, considering that the hollow needle N contacts the deformed tube portion 115, the total length of the to-be-plugged portion 113 and the connection tube portion 114 is preferably set to be longer than the length of the hollow needle N.

In the first and second embodiments, the body portion 111 and the to-be-sealed portion 112 are integrally molded together. However, the present invention is not necessarily limited to this. For example, the body portion 111 and the to-be-sealed portion 112 may be separately formed and then connected together. Accordingly, the body portion 111 and the to-be-sealed portion 112 are not necessarily made of the same material, but the body portion 111 and the to-be-sealed portion 112 are made of different materials and then connected together. When the body portion 111 and the to-be-sealed portion are made of different materials, for example, the body portion 111 is made of a material having a high rigidity and the to-be-sealed portion 112 is made of a soft material, which enables the to-be-sealed portion 112 to be radially deformed while at the same time ensuring the rigidity of the body portion 111. Thus, the port member 11 similar to the second embodiment may be formed.

In the first and second embodiments, the to-be-plugged portion 113 is larger in diameter than the connection tube portion 114 to have the body portion 11 formed into a rod shape with a stepped portion. However, the present invention is not necessarily limited to this. For example, the to-be-plugged portion 113 and the connection tube portion 114 may have the same size. However, since the to-be-plugged portion 113 is plugged by the plug member 110, it is a matter of course that the size is determined to allow the to-be-plugged portion 113 to sealingly receive the plug member 110 which has a size enabling the hollow needle N to be smoothly pierced thereinto.

Figure 10A:
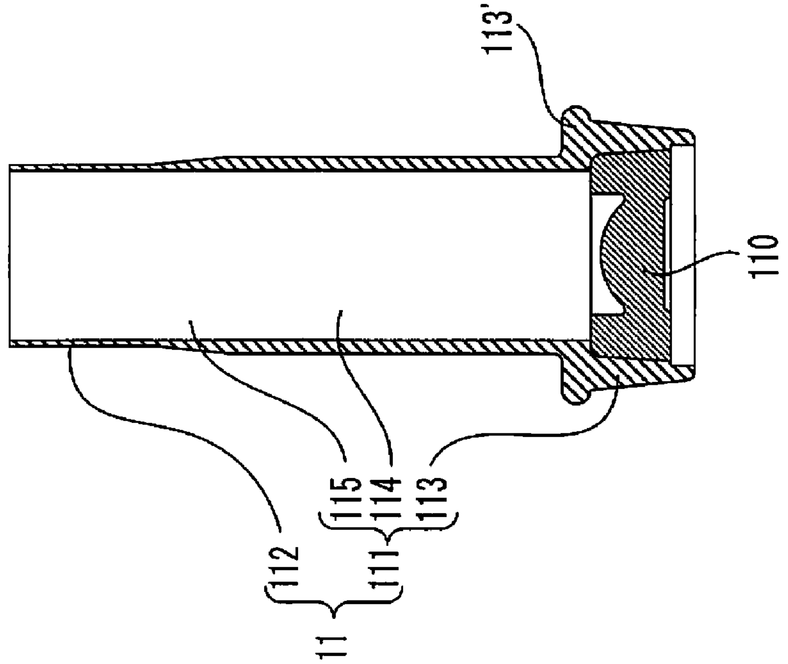
FIGS. 10(*a*) and 10(*b*) are vertical cross sectional views of still another embodiment of the present invention, in which FIG. 10(*a*) is a vertical cross sectional view of a port member having a to-be-sealed portion smaller in outer diameter than a connection tube portion, and FIG. 10(*b*) is a vertical cross sectional view of a port member having- a to-be-sealed portion larger in inner diameter than a connection tube portion and smaller in outer diameter than the connection tube portion.
Figure 10B:
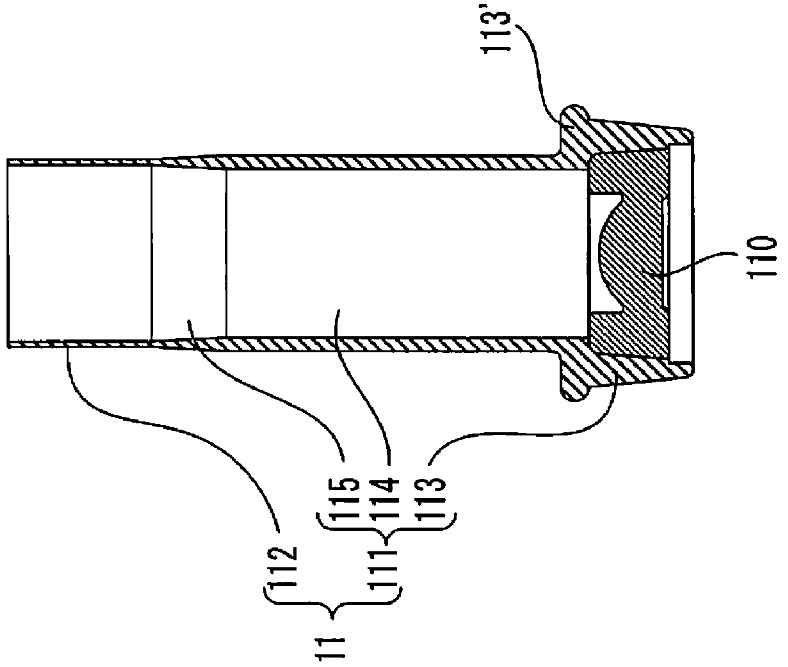
Figure 11B:
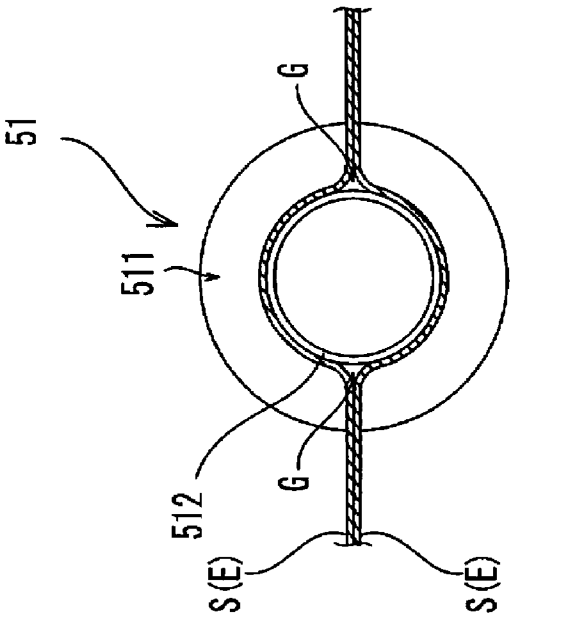
FIGS. 11(*a*) and 11(*b*) are cross sectional views of a conventional infusion bag, in which FIG. 11(*a*) is a front view with a part of the bag body omitted, and FIG. 11(*b*) is a vertical cross sectional view for explaining a sealed state of the port member and the bag body (resin sheets).
Figure 11A:
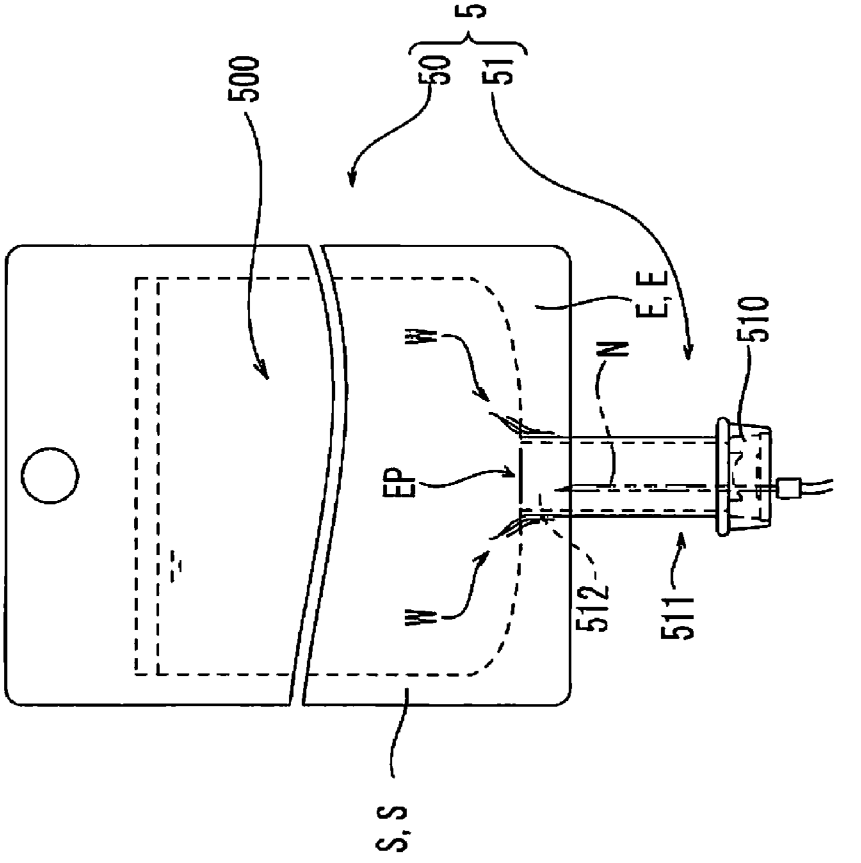

In the second embodiment, the connection tube portion 114, the deformed tube portion 115 and the to-be-sealed portion 112 have the same outer diameter, while the inner diameter of the to-be-sealed portion 112 is larger than the inner diameter of the connection tube portion 114, thereby forming the to-be-sealed portion 112 with a thinner wall than the connection tube portion 114. However, the present invention is not necessarily limited to this. For example, it is possible to employ an arrangement, in which the inner diameter of the to-be-sealed portion 112 is the same as the inner diameter of the connection tube portion 114, while the outer diameter of the to-be-sealed portion 112 is smaller than the outer diameter of the connection tube portion 14 to have a thickness of the to-be-sealed portion thinner than the connection tube portion 114, as shown in FIG. 10(*a*), or an arrangement, in which the inner diameter of the to-be-sealed portion 112 is larger than the inner diameter of the connection tube portion 114, while the outer diameter of the to-be-sealed portion 112 is smaller than the outer diameter of the connection tube portion 114 to have a thickness of the to-be-sealed portion 112 thinner than the connection tube portion 114, as shown in FIG. 10(*b*). In the first and second embodiments, the deformed tube portion 115 is formed to become thinner as it advances towards the to-be-sealed portion 112. However, the present invention is not necessarily limited to this. For example, the deformed tube portion 115 may be formed to be continued with the to-be-sealed portion 112 (to be the same as the to-be-sealed portion 112 in both the outer diameter and the inner diameter).

That is, the deformed tube portion 115 may be formed to be deformable in conformity with the deformation of the to-be-sealed portion 112. However, as described in the second embodiment, the deformed tube portion 115 has a portion close to the connection tube portion 14 having a cylindrical tube shape, and a portion close to the to-be-sealed portion 112 having a flattened tube shape (a shape having an inner hole decreasing). Therefore, when the total length of the to-be-plugged portion 113 and the connection tube portion 114 is set to be equal to or shorter than the length of the hollow needle N, the likelihood of contacting of the leading end of the hollow needle N is increased depending on the pierced amount of the hollow needle N or the position of the hollow needle N pierced through the plug member 110. Therefore, when the deformed tube portion 115 is entirely formed with a thin wall, the leading end of the hollow needle N, which has been pierced through the plug member 110 and contacted the deformed tube portion 115, is easy to be pierced therethrough. In view of this, in the same manner as the aforesaid embodiments, it is preferable to employ an arrangement, in which the total length of the to-be-plugged portion 113 and the connection tube portion 114 is set to be longer than the length of the hollow needle N so as not to allow the leading end of the hollow needle N pierced through the plug member 110 to reach the deformed tube portion 115, or the connection tube portion 114 is formed with a thick wall as much as possible, while at the same time enabling the deformation of the to-be-sealed portion 112, thereby preventing the hollow needle N from being pierced through the deformed tube portion 115.

The invention claimed is:

1. A port member for an infusion solution bag comprising a tubular body portion having one end plugged by a plug member structured to enable a hollow needle to be pierced into the plug member, and a tubular to-be-sealed portion continuously formed with an other end of the body portion and having an inner space communicated with the inside of the body portion, the to-be-sealed portion being held between and sealed to end portions of resin sheets overlapped together to form a bag body having an inner space for accommodation of at least a medicine, the tubular body portion comprising a to-be-plugged portion having a tube shape and being structured to be plugged by the plug member, a connection tube portion having a cylindrical tube shape continuously formed with the to-be-plugged portion and having an inner space communicated with the inside of the to-be-plugged portion, and a deformed tube portion for connection between the connection tube portion and the to-be-sealed portion in communication with each other, the deformed tube portion having a shape changing from a cylindrical shape to a flattened tube shape having a minor axis and a major axis as it advances from one end to the other end, in which the minor axis is smaller than the outer diameter of the connection tube portion, and the to-be-sealed portion thus sealed has a radially flattened shape.

2. A port member for an infusion solution bag comprising a tubular body portion having one end plugged by a plug member structured to enable a hollow needle to be pierced into the plug member, and a tubular to-be-sealed portion continuously formed with an other end of the body portion and having an inner space communicated with the inside of the body portion, the to-be-sealed portion being held between and sealed to end portions of resin sheets overlapped together to form a bag body having an inner space for accommodation of at least a medicine, the tubular body portion comprising a to-be-plugged portion having a tube shape and being structured to be plugged by the plug member, a connection tube portion having a cylindrical tube shape continuously formed with the to-be-plugged portion and having an inner space communicated with the inside of the to-be-plugged portion, and a deformed tube portion for connection between the connection tube portion and the to-be-sealed portion in communication with each other, the deformed tube portion having a shape deformable from a cylindrical shape to a flattened tube shape having a minor axis and a major axis as it advances from one end to the other end, in which the minor axis is smaller than the outer diameter of the connection tube portion, and the to-be-sealed portion thus sealed is radially deformable from a cylindrical shape to a flattened tube shape.

3. The port member for an infusion solution bag according to claim 2, wherein the to-be-sealed portion is formed with a thinner wall than the body portion to be radially deformable.

4. The port member for an infusion solution bag according to any one of claims 1 to 3, wherein a length of the body portion between one end and another end is preferably longer than an entire length of the hollow needle.

5. The port member for an infusion solution bag according to claim 1, wherein the body portion and the plug member are formed by double molding.

6. An infusion solution bag comprising a bag body formed with resin sheets overlapped and sealed together along end portions of the resin sheets, thereby forming an inner space in the bag body for accommodation of at least a medicine, a port member fluidly connected to the bag body, the port member including a tubular body portion having one end plugged by a plug member structured to enable a hollow needle to be pierced into the plug member, and a tubular to-be-sealed portion continuously formed with an other end of the body portion and having an inner space communicated with the inside of the body portion, the to-be-sealed portion being held between and sealed to end portions of the resin sheets overlapped together, the tubular body portion comprising a to-be-plugged portion having a tube shape and being structured to be plugged by the plug member, a connection tube portion having a cylindrical tube shape continuously formed with the to-be-plugged portion and having an inner space communicated with the inside of the to-be-plugged portion, and a deformed tube portion for connection between the connection tube portion and the to-be-sealed portion in communication with each other, the deformed tube portion having a shape changing from a cylindrical shape to a flattened tube shape having a minor axis and a major axis as it advances from one end to the other end, in which the minor axis is smaller than the outer diameter of the connection tube portion, and the to-be-sealed portion thus sealed has a radially flattened shape and is held between and sealed to the end portions of the resin sheets from opposite sides in a direction of a minor axis of the to-be-sealed portion.

7. The infusion solution bag according to claim 6, wherein a length of the body portion between one end and another end is longer than an entire length of the hollow needle.

8. The port member for an infusion solution bag according to claim 2, wherein the body portion and the plug member are formed by double molding.

9. The port member for an infusion solution bag according to claim 3, wherein the body portion and the plug member are formed by double molding.

* * * * *